United States Patent [19]

Huc et al.

[11] Patent Number: 5,331,092
[45] Date of Patent: Jul. 19, 1994

[54] PROCESS OF PREPARATION OF COLLAGEN CONTAINING IN MAJOR PROPORTION INSOLUBLE COLLAGEN AND COLLAGEN HAVING HIGH MECHANICAL RESISTANCE AND THERMAL STABILITY OBTAINED THEREBY

[75] Inventors: Alain Huc, Ste. Foy les Lyons; René Gimeno, Pelussin, both of France

[73] Assignee: Coletica, Lyons, France

[21] Appl. No.: 971,636

[22] Filed: Nov. 6, 1992

[51] Int. Cl.$^5$ .................... C08L 89/06; A61L 15/04; A61K 9/22

[52] U.S. Cl. .................... 530/356; 435/240.25; 435/240.26; 435/174; 435/176

[58] Field of Search .................... 530/356

[56] References Cited

U.S. PATENT DOCUMENTS 4,280,954 7/1981 Yannas et al. .................... 260/123.7
4,863,856 9/1989 Dean, Jr. et al. .................... 435/68

FOREIGN PATENT DOCUMENTS 411124 2/1991 European Pat. Off. .
WO85/04413 10/1985 PCT Int'l Appl. .

*Primary Examiner*—Lester L. Lee
*Assistant Examiner*—P. Lynn Touzeau
*Attorney, Agent, or Firm*—Armstrong, Westerman, Hattori, McLeland & Naughton

[57] ABSTRACT

A process of preparation of collagen containing in major proportion insoluble collagen is disclosed, including rinsing and washing the collagenic tissue, acidifying the ground material pH value 1 to 4 to get a collagenic paste which is diluted in a diluting solution to get the collagen gel having a concentration in collagen lower than about 2.5 by weight expressed in dry collagen, and performing a shearing stirring at high speed producing ultrasonic effect to get a substantially homogeneous collagenic gel. The collagen has improved mechanical resistance and thermal stability.

17 Claims, No Drawings

PROCESS OF PREPARATION OF COLLAGEN CONTAINING IN MAJOR PROPORTION INSOLUBLE COLLAGEN AND COLLAGEN HAVING HIGH MECHANICAL RESISTANCE AND THERMAL STABILITY OBTAINED THEREBY

The invention essentially relates to a process of preparation of collagen containing a major proportion of insoluble collagen and collagen, containing in major proportion insoluble collagen, thereby obtained as a new material. The invention more precisely provides a collagenic material under pure and native form, which is easily workable under physiological conditions and which may be free from any biological contamination, according to a preferred embodiment although the collagenic raw material may initially be biologically contaminated and therefore, the invention enables to manufacture a very valuable collagenic material which can be used to manufacture notably hemostatic products like hemostatic pads and hemostatic sponges.

Recently, the problems resulting from the blood contamination particularly by the AIDS virus and hepatitis virus required from the physician and notably the surgeon lower as much as possible the blood losses during surgical operations.

Therefore the use of improved hemostatic products, like hemostatic pads and hemostatic sponges become more and more important.

SUMMARY OF THE PRIOR ART

In the prior art, the substances which have been known to be used as hemostatic pads, are usually: gelatin, oxidated cellulose, thrombin, collagen. Collagen is known to have the highest hemostatic capacity.

Therefore, the collagen based pads are promising but up to now those products available on the market have known limited success due to the difficulty of handling these materials.

As a matter of fact, the putting in place and the eventual withdrawal of the collagenic pads available on the market is difficult and is mainly limited by the physiological conditions of a surgical operation, namely a temperature of about 37° C. and a wet medium resulting mainly from blood loss.

SUMMARY OF THE INVENTION

The main object of the present invention is to solve the new technical problem of providing a collagen having improved mechanical resistance and improved thermal stability, thereby being more easily usable by a clinician, notably a surgeon, in the physiological conditions while keeping all the hemostatic properties of the collegen protein.

Another main purpose of the invention is to provide a collagen of an improved mechanical property and thermal stability, said collagen containing in major proportion insoluble collagen. In the present description and claims major proportions mean more than 50% of insoluble collagen.

Another main purpose of this invention is to provide a collagen having improved mechanical resistance and improved thermal stability having at least 80% by weight of insoluble collagen.

Another main purpose of the present invention is to provide a method of preparation of collagen having improved mechanical resistance and improved thermal stability, according to very simple processing steps, enabling the manufacture of large volumes, thereby providing a process usable on an industrial scale.

Further a main purpose of that invention is to provide a collagen and a method for its preparation, enabling to provide collagen free from any biological contamination such as viruses, bacteria and so on.

Another main purpose of this invention is to provide a collagen and a process for its preparation, substantially non-dereticulated, namely having preferably an average reticulation proportion higher then 70% by weight. The collagen is accordingly in essentially native form.

All these technical problems have been solved for the first time in that invention in a very simple way, thereby being usable on the industrial scale.

Therefore, according to the first aspect, the present invention provides a method of preparation of collagen containing a major proportion of insoluble collagen substantially not dereticulated, from collagenic tissue, comprising grinding and washing said collegenic tissue at least by phosphate buffer and water to get a ground material; acidifying said ground material to a pH value ranging between 3 and 4, so as to reach a collagenic paste which is then diluted in a diluting solution to get a collagenic gel having a collagen concentration lower than about 2.5% by weight expressed in dry collagen; and performing an homogenizing shearing stirring at high speed producing ultrasonic effect, during a period of time sufficient to get a substantially homogeneous collagen gel containing in major proportion insoluble collagen.

According to a preferred embodiment, said homogeneous collagen gel is dried.

According to a particular embodiment, said drying can be performed by evaporation notably to get a collagen film.

According to another particular embodiment, said drying comprises a freeze-drying also named lyophilization, notably when it is wished to prepare a pad or a sponge.

According to another advantageous embodiment of the invention, after drying, said process comprises performing a cross-linking or reticulation of said collagen without any chemical treatment blocking the side groups of collagen.

Preferably, said cross-linking or reticulation is performed by a physical means which does not alter the chemical structure of said collagen. Most preferably, said cross-linking or reticulation of the collagen gel comprises the heating of said collagen gel under vacuum. According to a particular feature, said vacuum is a vacuum having a pressure value lower than 1 mbar, in particular lower than about 500 microbars.

According to another specific feature, the heating under vacuum, is performed at a heating temperature higher than 80° C. and more preferably at about 110° C.

According to another specific feature, said heating under vacuum is performed during a period of time ranging between about 1 hour and about 24 hours.

According to a particularly advantageous embodiment of the invention, after grinding the collegenic tissue, and prior to said acidifying step, a biological decontamination treatment is performed on said collagen.

According to a preferred embodiment, said biological decontamination treatment comprises a treatment in a soda bath, at room temperature, at a sufficient soda concentration and during a period of time sufficient to perform said biological decontamination without affecting the structure of said collagen.

According to the best embodiment, said decontamination treatment is performed in a bath of soda 1N, during one hour at room temperature, namely around 20° C.

According to a further embodiment, the collagen gel can be molded into a shape which is directly industrially usable. Accordingly, it can be molded as a film shape which is then dried.

And, it can be molded into a pad or a sponge, and in such a case it is preferably freeze-dried or lyophilized.

According to a second aspect, the present invention provides a collagen containing in major proportion insoluble collagen, said collagen being substantially not dereticulated, having improved mechanical resistance and improved thermal stability, said collagen when cross-linked by physical means not altering the chemical structure of said collagen having preferably a beginning-of-denaturation temperature higher than 34° C. and an end-of-denaturation temperature higher than 57° C. and more preferably higher than 59° C. and a break strength, expressed in Newtons, of at least 1 of a non-sterile collagen sample in the humid state having a thickness of 6 mm and a width of 15 mm.

Preferably, said collagen comprises at least 70% by weight of insoluble collagen.

According to a preferred feature, said collagen comprises at least 80% insoluble collagen and most preferably between 80 and 90% by weight of insoluble collagen, the remaining being acid soluble collagen.

According to another particular feature, said collagen has been obtained by an acid treatment at a pH ranging between 3 and 4 of the ground material resulting from grinding and washing collagenic tissue, to get a collagenic paste which is diluted in a diluting solution to get a collagen gel having a concentration in collagen lower than about 2.5% by weight expressed in dry collagen, and finally an homogenizing shearing stirring at high speed producing ultrasonic effect during a period of time sufficient to get a substantially homogeneous collagenic gel.

Other features of said collagen material purely result from the above description made with regard to the process, for one skilled in the art.

Furthermore, collagen which is used according to the present invention is preferably collagen of type I or of type III.

According to another advantageous embodiment, the collagen is coming from an animal skin and notably from a bovide skin, in particular calf skin or bovine skin.

According to another specific embodiment, said acidifying step is performed with a weak organic acid, and preferably acetic acid.

According to another specific embodiment, said stirring providing ultrasonic effect is performed with a device providing a peripheral speed ranging between about 15 and 21 meters per second. The flowrate of said gel may advantageously be about 100 liters per hour. This device is preferably of the Ultraturex type UTL 115/-6 marketed by IKA, wellknown to those skilled in the art.

Other features and advantages of the present invention will appear clearly from the following detailed description of the invention made with reference to specific examples given only by way of illustration and which cannot limit the scope of the invention. These examples constitute an integral part of the invention.

All the percentages are expressed by weight unless otherwise stated.

DETAILED DESCRIPTION OF THE INVENTION

Invention Example 1

Preparation of a collagen gel having improved mechanical resistance and thermal stability.

1) Preparation of purified dermis

The skin of freshly slaughtered calves is washed for 2 hours in a container.

Then the skin is subjected to chemical depilation in a bath containing 400 g of skin (dry material: about 30%):
250 ml of water.
2.5 g of ammonium sulphide at 60%.
3.5 g of lime.

This bath is subjected to a rotation for 30 minutes at 4 rpm.

The total duration of the depilation lasts 36 hours.

The depilated skin is then isolated from the rest of the skin by a slitting operation using a rotating bandsaw. This treatment enables to get the dermis which is collected and to eliminate the other tissues.

Lime treatment:

The depilated skin is then placed in a bath containing 400 g of skin:
50 ml of water
3 g of ammonium chloride
0.5 g of sodium metabisulphite.

The bath is agitated by rotating it for about two hours and thirty minutes.

The salts are eliminated by two successive washings with water, of 15 minutes' duration each, at a ratio of 100 g of skin for 200 ml of water.

2) Grinding

The treated dermis is then ground and extruded through a grid having a hole diameter of 5 mm, thereby getting a ground preparation.

3) Washing of the ground preparation

The ground preparation is washed in apyrogenic purified water at a ratio of 1 kg of ground preparation for 5 l of water. It is then washed with a phosphate buffer at pH 7.8 under stirring during one hour, in a stainless tank at a ratio of 1 kg of ground preparation for 5 l of buffer ($Na_2HPO_4$: 21.7 g per liter and $KH_2PO_4$ 2.0.78 g per liter). This washing is performed twice.

The ground preparation is separated from the supernatant by continuous centrifugation in a centrifuge rotating machine at 4000 rpm (Centrifuge rotating machine named "Decanteuse Rousselet"). The phosphate is eliminated in the same conditions by two successive washings with apyrogenic purified water: 1 kg of ground material, 5 l of water, 1 hour of stirring, centrifugation.

4) Preparation of the collagen gel

The ground material is then acidified with acetic acid to bring the pH to a value ranging between 3 and 4. The amount of acid is preferably of 5% by weight with regard to the collagen expressed in dry materials, and the final dilution expressed in dry collagen is of 10% by weight. The final molarity is of about 0.08M in acetic acid.

The whole solution is stirred and malaxed for one hour in an helical malaxer, to get a paste which is diluted with apyrogenic purified water to get a gel having a concentration varying as a function of the product to be prepared and preferably ranging between 0.7 and about 2% by weight of collagen with regard to the total weight of the composition.

5) The homogenizing with shearing stirring at high speed producing ultrasonic effect This diluted gel is homogenized by subjecting it to an homogenizing treatment in an apparatus named Ultraturax-in line marketed by the firm IKA capable of providing a shearing stirring at high speed producing ultrasonic effect. This machine is of the type UTL T 115/-6 having a peripheral speed settable to between 15 and 21 meters per second. The gel flowrate can be set to be about 100 liters per hour.

All the ground preparation in diluted form, is passed in this ultrasonic homogenizer at said flowrate, thereby getting an homogenized collagen gel.

This gel contains a major proportion of insoluble collagen and usually between 80 and 90% of insoluble collagen and 10 to 20% of acid soluble collagen. This collagen gel is therefore different from the collagen materials obtained by other prior art processes which only contained acid soluble collagen.

This homogenized collagen can be used to manufacture hemostatic pads as follows:

6) Manufacture of hemostatic pads

The collagen gel as obtained hereinabove at a concentration of 0.72% weight/weight is molded within molds at sizes of sponges to be manufactured and freeze-dried.

The freeze-drying is preferably performed in a freeze-drier comprising a structure as disclosed in U.S. Pat. No. 4,953,299 granted on Sep. 4, 1990. Between the lyophilization plates, heating screens are present which enable the freezing of the gel paste thereby reaching pads which have horizontal and regular surfaces.

The freezing is performed at about −30° C. and then the heating is performed at 32° C.

The freeze-drying lasts in total 16 hours and the drying is performed at a pressure of 400 microbars.

7) Cross-linking or reticulation of the collagen

The collagenic pads, obtained after freeze-drying, are placed for 10 hours in an oven maintained at a vacuum pressure of 400 microbars and heated to a temperature of 110° C.

This heat treatment under vacuum provides a cross-linking of the collagen.

8) Conditioning

The cross-linked collagen pads are then conditioned as usual in double blister of copolyester resin.

9) Sterilization

The product can be as usual sterilized under beta irradiation at a dose of 15 KGy.

The non cross-linked and non-sterile collagen, under the form of a hemostatic pad which is obtained by the end of step 6 hereabove after freeze-drying, when cut as a sample having a thickness of 6 mm and a width of 15 mm, in the humid form by being re-wetted, has a break strength in Newtons of 0.52±0.17. An identical sample of an acido soluble collagen pad obtained according to the same freeze-drying procedure has a break strength in Newtons of 0.27±0.11.

Accordingly, the invention enables to improve by about 100% the break strength of the collagen, which is remarkable.

Furthermore, when the invention collagen is cross-linked under the cross-linking conditions of hereabove step 7), prior to sterilization, the break strength becomes 1.91±0.22, which has to be compared with the acido soluble collagen pad which, when cross-linked in the above conditions, has a break strength of 0.19±0.02 N.

On the other hand, when the invention collagen is cross-linked and has been sterilized under beta irradiation at a dose of 15 KGy, namely as obtained after step 9) hereabove, the temperature of the beginning-of-denaturation is of 34.2° C., the peak of denaturation is of 41.8° C. and the temperature of end-of-denaturation is of 60.0° C., which values have to be compared with cross-linked and sterilized acido soluble collagen which has a temperature of beginning-of-denaturation of 32.4° C., a peak of denaturation of 39.0° C. and a temperature of end-of-denaturation of 54.7° C.

These experiments show that the cross-linking procedure improves in a very important way the mechanical properties of the collagen material prepared according to the invention and which contains a major portion of insoluble collagen and that this cross-linking procedure has no effect on the mechanical properties of acido soluble collagen material.

The above comparative tests also point out that the invention collagen is much more resistant than the acido soluble collagen and that its thermal stability is higher.

A chemical analysis has been performed of the collagen hemostatic pad after cross-linking prior to sterilization as obtained after step 6) hereabove, which chemical analysis is given in Table I, herebelow.

TABLE I

COLLAGEN HEMOSTATIC PAD OBTAINED AFTER STEP 6
Chemical Analysis

| The results are given in g for 100 g of product. | |
|---|---|
| • Dry matter | 86 |
| • Mineral matter | 0.15 |
| • Nitrogen | 16.0 |
| • Total protein (after nitrogen) | 85.7 |
| • Hydroxyproline | 11.2 |
| • Collagen (after hydroxyproline) | 84.0 |
| • Acidity (in acetic acid) | 0.65 |

The thermal stability is measured in a scanning differential calorimeter of Trademark Setaram which enables to record, in relation to the temperature, the heat amount necessary to get thermal denaturation of the collagenic pad and to get a denaturation peak.

Due to this denaturation peak, it is possible to determine the temperature of the beginning of denaturation, the temperature of the denaturation peak, as well as the temperature of the end of denaturation.

Finally, this technology also makes it possible to measure the amount of heat necessary to get the thermal denaturation which is directly related to the ratio of collagenic native structure contained in the hemostatic pad. It is expressed in Joules per mg of collagen.

With the invention collagen, the Enthalpy of denaturation is of $4.8 \times 10^{-2}$ J/mg of collagen after cross-linking and prior to sterilization.

Invention Example 2

Preparation of collagen biologically decontaminated

1) Obtention of purified dermis and its grinding

The steps for obtaining purified dermis and for grinding same are identical to those in Example 1.

After said two first steps, it is performed a biological decontamination as follows:

2) Biological decontamination

The ground preparation is placed in a solution of soda 1.5 N at a ratio of 900 g for 1.8 l of solution at a concentration of 1 mole of soda per liter. It is homogenized with a planetary stirrer maintained at 20° C., and left to stay for one hour. After this period of time, it is performed a dilution with 4.5 l of sterile permuted water for 1 liter of suspension of ground preparation in soda.

After decantation with the use of a continuous centrifugating device as that used in Example 1, the ground preparation is gathered and manufacture of the hemostatic pad follows as set forth in Example 1 from Step 3) to the end including Step 9).

It is extremely important to determine that the decontamination treatment does not lower the denaturation temperature of the invention cross-linked and sterile collagen.

The thermal stability of the invention collagen after Example 2 is compared with the invention collagen as obtained in Example 1 (namely prior to decontamination), the test results being reported in Table II.

The enzymatic digestion test results are reported in Table III.

TABLE III

| Time (in hour) | Invention cross-linked and sterile collagen pad as obtained in Ex. 1 | Pad after sodium hydroxyde treatment Percentage of degradation |
| --- | --- | --- |
| 1 | 8.70 | 8.0 |
| 3 | 27.1 | 25.8 |
| 5 | 68.9 | 69.2 |
| 7 | 83.1 | 81.7 |
| 9 | 91.6 | 92.1 |
| 24 | 100 | 100 |

It can be observed from Table II that the decontamination treatment does not affect the thermal resistance of the collagen according to the invention. Further, the decontamination treatment does not affect the resistance of the invention collagen to enzymatic digestion as shown in Table III. As a consequence, the decontamination treatment with sodium hydroxide has not modified the invention collagen, which constitutes an unexpected result for one skilled in the art.

Invention Example 3

Preparation of a pad for the treatment of soft tissues, particularly skin and gengiva, made of collagen containing an active substance.

It is at first prepared a collagen gel according to Steps 1) to 4) described in Example 1.

TABLE II

| Temperature | Invention cross-linked and sterile collagen pad as obtained in Ex. 1 | Invention cross-linked sterile collagen pad after decontamination with sodium hydroxide treatment as obtained in Ex. 2 |
| --- | --- | --- |
| beginning of denaturation | 34.2° C. | 34.4° C. |
| peak | 41.8° C. | 41.4° C. |
| end of denaturation | 60.0° C. | 60.02° C. |
| enthalpy of denaturation | $5.62.10^{-2}$ | $5.76.10^{-2}$ |

It is also important to determine that the collagen which has been biologically decontaminated has the same behavior with regard to enzymatic digestion by the collagenase present in the body of live beings like mammals, including humans.

Accordingly, a comparative test has been performed between the invention cross-linked and sterile collagen pad as obtained in Example I as compared with the invention cross-linked sterile collagen pad after decontamination with sodium hydroxide treatment as obtained in Example II with regard to the resistance to degradation test by bacterial collagenase.

The enzymatic denaturation or digestion test is performed in a dialysis tube containing the hemostatic pad in presence of bacterial collagenase from sigma, reference C6885, at a concentration of 50U/ml in a buffer medium and placing this tube within the same buffered medium (Buffer: 10 mM Tris, 25 mM $CaCl_2$, pH; 7.4).

The compared results obtained with the collagen pad non-treated and treated by soda solution show that their enzymatic digestions are almost identical. From this experiment it can be concluded that the soda treatment described above has not modified the collagen.

The enzymatic digestion of the pad is followed through a dosage in relation to the time of liberated hydroxyproline in the dialysis bath. Hydroxyproline is dosed according to the method described by Stegeman et al. in K. Clin. Chim. Acta. (1967) 18, 27).

Then, to the collagen gel is added an active substance, for example an antibiotic substance, here for instance 0.5% by weight of tetracycline based on the weight of collagen.

Then it is proceeded as set forth in Example 1 from Step 5) to Step 9) to get a cross-linked sterile collagen pad containing an antibiotic substance, here tetracycline.

Of course, instead of an antibiotic substance, it can be used an antiseptic, one or several polysaccharides, including a muccopolysaccharide, one or several hydrophilic proteins such as albumine, lactalbumine. These active substantce can be used in mixture, as is understandable for one skilled in the art.

What is claimed is:

1. A method of preparation of collagen from collagenic tissue, comprising grinding and optionally washing said collagenic tissue with a phosphate buffer and then with purified water to eliminate the phosphate, to get a ground material; acidifying said ground material to a pH value ranging between 3 and 4, so as to obtain a collagenic paste which is then diluted in a diluting solution to get a collagenic gel having a collagen concentration lower than 2.5% by weight expressed in dry collagen; and performing an homogenizing shearing stirring at high speed providing ultrasonic effect during a period of time sufficient to get a substantially homogeneous collagen gel containing in major proportion insoluble collagen.

2. The method of claim 1, wherein said homogeneous collagen gel is dried.

3. The method of claim 2, wherein said drying is performed by evaporation.

4. The method of claim 2, wherein said drying comprises a freeze-drying.

5. The method of claim 2, comprising, after drying, performing a cross-linking of said collagen.

6. The method of claim 5, wherein said cross-linking is performed by a physical means not altering the chemical structure of said collagen.

7. The method of claim 5, wherein said cross-linking comprises heating said collagen gel under vacuum.

8. The method of claim 7, wherein said vacuum is a vacuum having a pressure value lower than 1 millibar.

9. The method of claim 8, wherein said heating under vacuum is performed at a heating temperature higher than 80° C. and during a period of time ranging between about 1 hour and about 24 hours.

10. The method of claim 1, wherein after grinding the collagenic tissue and prior to said acidifying step, a biological decontamination treatment is performed on said collagen.

11. The method of claim 10, wherein said biological decontamination treatment comprises a treatment in a soda bath, at room temperature, at a sufficient soda concentration and during a period of time sufficient to perform said biological decontamination without affecting the chemical structure of said collagen.

12. The treatment of claim 11, wherein said decontamination treatment is performed in a bath of soda 1N, during one hour at room temperature.

13. The method of claim 1, wherein the collagen gel is subsequently molded into a shape.

14. The method of claim 1, wherein a minimum concentration of said collagen in said collagenic gel is 0.7% by weight.

15. The method of claim 3, wherein said evaporation produces a collagen film.

16. The method of claim 4, wherein a pad or sponge is prepared from freeze-dried collagen.

17. The method of claim 1, wherein said purified water is apyrogenic.

* * * * *